(12) United States Patent
Talon

(10) Patent No.: US 10,130,780 B2
(45) Date of Patent: Nov. 20, 2018

(54) DETECTION OF AEROSOL-FORMING SUBSTRATE IN AN AEROSOL GENERATING DEVICE

(71) Applicant: PHILIP MORRIS PRODUCTS S.A., Neuchatel (CH)

(72) Inventor: Pascal Talon, Thonon-les-Bains (FR)

(73) Assignee: Philip Morris Products S.A., Neuchatel (CH)

( * ) Notice: Subject to any disclaimer, the term of this patent is extended or adjusted under 35 U.S.C. 154(b) by 444 days.

(21) Appl. No.: 14/361,142

(22) PCT Filed: Dec. 28, 2012

(86) PCT No.: PCT/EP2012/077063
§ 371 (c)(1),
(2) Date: May 28, 2014

(87) PCT Pub. No.: WO2013/098396
PCT Pub. Date: Jul. 4, 2013

(65) Prior Publication Data
US 2014/0345606 A1 Nov. 27, 2014

(30) Foreign Application Priority Data
Dec. 30, 2011 (EP) .................................. 11196227

(51) Int. Cl.
*A61M 15/06* (2006.01)
*A61M 15/00* (2006.01)
(Continued)

(52) U.S. Cl.
CPC ....... *A61M 16/0051* (2013.01); *A24F 47/008* (2013.01); *A61M 11/00* (2013.01);
(Continued)

(58) Field of Classification Search
CPC .... A61M 15/06; A61M 15/00; A61M 15/009; A61M 15/0091; A61M 11/041;
(Continued)

(56) References Cited

U.S. PATENT DOCUMENTS 4,947,874 A * 8/1990 Brooks ................. A24F 47/008
128/202.21
5,372,148 A * 12/1994 McCafferty .......... A24F 47/008
128/202.21
(Continued)

FOREIGN PATENT DOCUMENTS

CN         1122213 A     5/1996
CN     101977522 A     2/2011
(Continued)

OTHER PUBLICATIONS

Extended European Search Report dated Jun. 1, 2012 in Patent Application No. 11196227.0.
(Continued)

*Primary Examiner* — Rachel T Sippel
*Assistant Examiner* — Tu Vo
(74) *Attorney, Agent, or Firm* — Oblon, McClelland, Maier & Neustadt, L.L.P.

(57) ABSTRACT

There is provided an aerosol generating device, including a heater element configured to heat an aerosol-forming substrate; a power source connected to the heater element; and a controller connected to the heater element and to the power source, wherein the controller is configured to control the power supplied to the heater element from the power source to maintain the temperature of the heater element at a target temperature, and is configured to compare a measure of power supplied to the heater element or energy supplied to the heater element from the power source to a threshold measure of power or energy to detect the presence of an
(Continued)

aerosol-forming substrate close to the heater element or a material property of an aerosol-forming substrate close to the heater element.

13 Claims, 4 Drawing Sheets

(51) Int. Cl.
| | |
|---|---|
| *A61M 11/00* | (2006.01) |
| *A24F 47/00* | (2006.01) |
| *A61M 16/00* | (2006.01) |
| *A61M 11/04* | (2006.01) |
| *A61M 16/10* | (2006.01) |
| *G01B 21/16* | (2006.01) |

(52) U.S. Cl.
CPC ......... *A61M 11/041* (2013.01); *A61M 11/042* (2014.02); *A61M 15/06* (2013.01); *A61M 16/0003* (2014.02); *A61M 16/024* (2017.08); *A61M 16/109* (2014.02); *G01B 21/16* (2013.01)

(58) Field of Classification Search
CPC ............ A61M 11/042; A61M 15/0021; A61M 15/0023; A61M 15/0025; A61M 15/0026; A24F 47/00; A24F 47/002; A24F 47/004; A24F 47/006; A24F 47/008
USPC .............. 374/5, 45; 219/494, 483–487, 497; 131/329, 273, 330
See application file for complete search history.

(56) References Cited

U.S. PATENT DOCUMENTS

| | | | | |
|---|---|---|---|---|
| 5,388,594 | A * | 2/1995 | Counts | A24F 47/008 128/202.21 |
| 5,498,855 | A * | 3/1996 | Deevi | A24F 47/008 131/194 |
| 5,499,636 | A * | 3/1996 | Baggett, Jr. | A24F 47/008 131/194 |
| 5,505,214 | A * | 4/1996 | Collins | A24F 47/008 128/202.21 |
| 5,530,225 | A * | 6/1996 | Hajaligol | A24F 47/008 131/194 |
| 5,591,368 | A * | 1/1997 | Fleischhauer | A24F 47/008 131/194 |
| 5,613,504 | A | 3/1997 | Collins et al. | |
| 5,665,262 | A * | 9/1997 | Hajaligol | A24F 47/008 131/194 |
| 5,666,978 | A * | 9/1997 | Counts | A24F 47/008 131/194 |
| 5,692,291 | A | 12/1997 | Deevi et al. | |
| 5,692,525 | A * | 12/1997 | Counts | A24F 47/008 131/194 |
| 5,730,158 | A | 3/1998 | Collins et al. | |
| 5,865,185 | A | 2/1999 | Collins et al. | |
| 5,878,752 | A * | 3/1999 | Adams | A24F 47/008 131/194 |
| 5,902,501 | A * | 5/1999 | Nunnally | A24F 47/008 219/263 |
| 5,954,979 | A * | 9/1999 | Counts | A24F 47/008 131/194 |
| 6,040,560 | A * | 3/2000 | Fleischhauer | A24F 47/008 128/202.21 |
| 2002/0005207 | A1* | 1/2002 | Wrenn | A24C 5/478 131/194 |
| 2003/0154991 | A1* | 8/2003 | Fournier | A24F 47/008 131/194 |
| 2003/0226837 | A1* | 12/2003 | Blake | H05B 3/58 219/260 |
| 2004/0129280 | A1* | 7/2004 | Woodson | A24B 15/282 131/194 |
| 2006/0237002 | A1* | 10/2006 | Bonney | A61J 7/0472 128/200.23 |
| 2007/0045288 | A1* | 3/2007 | Nelson | A61M 11/041 219/533 |
| 2009/0095292 | A1* | 4/2009 | Hamano | A61M 15/0085 128/203.14 |
| 2009/0133472 | A1* | 5/2009 | Tada | G01N 27/18 73/31.05 |
| 2009/0133691 | A1* | 5/2009 | Yamada | A61M 11/041 128/200.16 |
| 2010/0089394 | A1* | 4/2010 | Sakurada | A61B 5/087 128/203.14 |
| 2010/0163063 | A1 | 7/2010 | Fernando et al. | |
| 2011/0265806 | A1* | 11/2011 | Alarcon | A24F 47/00 131/273 |

FOREIGN PATENT DOCUMENTS

| | | |
|---|---|---|
| CN | 102264251 A | 11/2011 |
| EA | 013849 B1 | 8/2010 |
| EP | 1 154 815 B1 | 7/2004 |
| EP | 1 827 146 B1 | 9/2009 |
| EP | 2 201 850 | 6/2010 |
| EP | 2 253 233 A1 | 11/2010 |
| JP | 2005-517421 A | 6/2005 |
| JP | 2011-515093 A | 5/2011 |
| JP | 2012-513750 A | 6/2012 |
| RU | 2 336 002 C2 | 10/2008 |
| WO | 2009 118085 | 10/2009 |

OTHER PUBLICATIONS

International Preliminary Report on Patentability and Written Opinion dated Jul. 1, 2014 in PCT/EP2012/077063.
International Search Report dated Jun. 24, 2013 in PCT/EP12/077063 Filed Dec. 28, 2012.
Combined Office Action and Search Report dated Aug. 25, 2015 in Chinese Patent Application No. 201280060088.5 (submitting English language translation only).
Office Action dated Sep. 15, 2016 in Russian Patent Application No. 2014131461(submitting English language translation only).
Office Action dated Oct. 19, 2016 in Japanese Patent Application No. 2014-549490 (submitting English language translation only).

* cited by examiner

DETECTION OF AEROSOL-FORMING SUBSTRATE IN AN AEROSOL GENERATING DEVICE

CROSS REFERENCE TO RELATED APPLICATION

This application is a national phase application based on PCT/EP2012/077063, filed on Dec. 28, 2012.

This specification relates to aerosol generating devices and in particular to aerosol generating devices for user inhalation, such as smoking devices. The specification relates to a device and method for detecting the presence or properties of an aerosol-forming substrate in an aerosol generating device in a cost effective and reliable way.

Conventional lit end cigarettes deliver smoke as a result of combustion of the tobacco and a wrapper which occurs at temperatures which may exceed 800 degrees Celsius during a puff. At these temperatures, the tobacco is thermally degraded by pyrolysis and combustion. The heat of combustion releases and generates various gaseous combustion products and distillates from the tobacco. The products are drawn through the cigarette and cool and condense to form a smoke containing the tastes and aromas associated with smoking. At combustion temperatures, not only tastes and aromas are generated but also a number of undesirable compounds.

Electrically heated smoking devices are known, which are essentially aerosol generating systems, which operate at lower temperatures than conventional lit end cigarettes. An example of such an electrical smoking device is disclosed in WO2009/118085. WO2009/118085 discloses an electrical smoking system in which an aerosol-forming substrate is heated by a heater element to generate an aerosol. The temperature of the heater element is controlled to be within a particular range of temperatures in order to ensure that undesirable volatile compounds are not generated and released from the substrate while other, desired volatile compounds are released.

It is desirable to provide a substrate detection function in an aerosol generating device, for example an aerosol generating device, in an inexpensive and reliable manner. Substrate detection is useful, for example, for preventing activation of a heater element when a substrate is not present and for preventing heating of unsuitable substrates.

In one embodiment there is provided an aerosol generating device comprising:
a heater element configured to heat an aerosol-forming substrate;
a power source connected to the heater element; and
a controller connected to the heater element and to the power source, wherein the controller is configured to control the power supplied to the heater element from the power source to maintain the temperature of the heater element at a target temperature, and is configured to compare a measure of power supplied to the heater element or energy supplied to the heater element from the power source to a threshold measure of power or energy to detect the presence of an aerosol-forming substrate close to the heater element or a material property of an aerosol-forming substrate close to the heater element.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may be a smoking device that interacts with an aerosol-forming substrate of an aerosol-generating article to generate an aerosol that is directly inhalable into a user's lungs thorough the user's mouth. An aerosol-generating device may be a holder.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. The term 'smoking article' is generally used hereafter. A smoking article may be, or may comprise, a tobacco stick.

The measure of power or energy can be any measure of power or energy, including average power over a predetermined time period or over a predetermined number of measurement cycles, a rate of change of power or energy or a cumulative measure of the power or energy supplied over a predetermined time period or over a predetermined number of measurement cycles.

In one embodiment, the measure of energy is normalised energy over a predetermined time period. In another embodiment, the measure of energy is a rate of decrease of normalised energy over a predetermined time period.

The amount of power or energy required to reach and maintain the heater element at a target temperature depends on the rate of heat loss from the heater element. This is strongly dependent on the environment surrounding the heater element. If a substrate is close to or contacts the heater element it will affect the rate of heat loss from the heater element compared to the situation in which there is no substrate close to the heater element. In one embodiment, the device is configured to receive an aerosol-forming substrate into contact with the heater element. The heater element then loses heat to the substrate by conduction. The device may be configured so that the substrate surrounds the heater element in use.

The controller may be configured to reduce to zero the supply of power to the heater element from the power source if the measure of power or energy is less than the threshold measure of power or energy. If the amount of energy needed to maintain the heater element temperature at a target temperature is less than expected, it may be because an aerosol forming substrate is not present in the device or it may be that an unsuitable substrate, such as a previously used substrate, is in the device. A previously used substrate will typically have lower water content and lower aerosol former content than a new substrate and therefore draws less energy from the heater element. In either case it is usually desirable to stop the supply of power to the heater.

The power source may be any suitable power supply, for example a DC voltage source, such as a battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate or a Lithium-Polymer battery. Power may be supplied to the heater element as a pulsed signal. The amount of power delivered to the heater element may be adjusted by altering the duty cycle or the pulse width of the power signal.

The controller may be configured to monitor the temperature of the heater element based on a measure of the electrical resistance of the heater element. This allows the temperature of the heater element to be detected without the need for additional sensing hardware.

The temperature of the heater may be monitored at predetermined time periods, such as every few milliseconds. This may be done continuously or only during periods when power is being supplied to the heater element.

The device may include a data output means and the controller configured to provide a record of the detected presence of an aerosol-forming substrate close to the heater element or a material property of an aerosol-forming substrate close to the heater element to the data output means. The substrate detection records may be useful to prevent inappropriate data from being used during clinical analysis. For example the aerosol generating device may include a wireless radio connected to the controller or a universal serial bus (USB) socket connected to the controller. Alternatively, the aerosol generating device may be configured to transfer data from the memory to an external memory in a battery charging device every time the aerosol generating device is recharged through suitable data connections. The device may be provided with special contacts for that purpose.

The device may also include a non-volatile memory. The controller may be configured to store substrate detection records in the memory. The memory may provide a temporary data store for the records, before they are passed to a larger more permanent external memory or directly to a data processing device.

In one embodiment, the controller is configured to provide a record of the detected presence of an aerosol-forming substrate close to the heater element or a material property of an aerosol-forming substrate close to the heater element to the data output means during a charging operation of the power source. The device may be connected to a charging device having a larger memory for longer term storage of the substrate detection records.

The device may be an electrical smoking device. The aerosol-generating device may be an electrically heated smoking device comprising an electric heater. The term "electric heater" refers to one or more electric heater elements.

The electric heater may comprise a single heater element. Alternatively, the electric heater may comprise more than one heater element. The heater element or heater elements may be arranged appropriately so as to most effectively heat the aerosol-forming substrate.

The electric heater may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics.

Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese-, gold- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Alternatively, the electric heater may comprise an infra-red heater element, a photonic source, or an inductive heater element.

The electric heater may take any suitable form. For example, the electric heater may take the form of a heating blade. Alternatively, the electric heater may take the form of a casing or substrate having different electro-conductive portions, or an electrically resistive metallic tube. Alternatively, one or more heating needles or rods that run through the centre of the aerosol-forming substrate may be as already described. Alternatively, the electric heater may be a disk (end) heater or a combination of a disk heater with heating needles or rods. Other alternatives include a heating wire or filament, for example a Ni—Cr (Nickel-Chromium), platinum, gold, silver, tungsten or alloy wire or a heating plate. Optionally, the heater element may be deposited in or on a rigid carrier material. In one such embodiment, the electrically resistive heater may be formed using a metal having a defined relationship between temperature and resistivity. In such an exemplary device, the metal may be formed as a track on a suitable insulating material, such as ceramic material, and then sandwiched in another insulating material, such as a glass. Heaters formed in this manner may be used to both heat and monitor the temperature of the heaters during operation.

The electric heater may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. In one embodiment, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a thermal conductor, such as a metallic tube.

The electric heater may heat the aerosol-forming substrate by means of conduction. In use, the electric heater may be at least partially in contact with the substrate, or the carrier on which the substrate is deposited. Alternatively, the heat from the electric heater may be conducted to the substrate by means of a heat conductive element.

In one embodiment, power is supplied to the electric heater until the heater element or elements of the electric heater reach a temperature of between approximately 250° C. and 440° C. Any suitable temperature sensor and control circuitry may be used in order to control heating of the heater element or elements to reach the temperature of between approximately 250° C. and 440° C., including the dual use heater discussed above. This is in contrast to conventional cigarettes in which the combustion of tobacco and cigarette wrapper may reach 800° C.

The controller may comprise a programmable microprocessor. In another embodiment, the controller may comprise a dedicated electronic chip such as a field programmable gate array (FPGA) or an application specific integrated circuit (ASIC). In general, any device capable of providing a signal capable of controlling a heater element may be used consistent with the embodiments discussed herein. In one embodiment the controller is configured to monitor a difference between the temperature of the heater element and the target temperature to detect a change in air flow past the heater element indicative of a user inhalation.

The aerosol forming substrate may be contained in a smoking article. During operation, the smoking article containing the aerosol-forming substrate may be completely contained within the aerosol-generating device. In that case, a user may puff on a mouthpiece of the aerosol-generating device. A mouthpiece may be any portion of the aerosol-generating device that is placed into a user's mouth in order to directly inhale an aerosol generated by the aerosol-generating article or aerosol-generating device. The aerosol is conveyed to the user's mouth through the mouthpiece. Alternatively, during operation the smoking article containing the aerosol-forming substrate may be partially contained within the aerosol-generating device. In that case, the user may puff directly on a mouthpiece of the smoking article.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length. The aerosol-forming substrate may be received in the sliding receptacle of the aerosol-generating device such that the length of the aerosol-forming substrate is substantially parallel to the airflow direction in the aerosol-generating device.

The smoking article may have a total length between approximately 30 mm and approximately 100 mm. The smoking article may have an external diameter between approximately 5 mm and approximately 12 mm. The smoking article may comprise a filter plug. The filter plug may be located at the downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise comminuting one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

In a particularly preferred embodiment, the aerosol-forming substrate comprises a gathered crimpled sheet of homogenised tobacco material. As used herein, the term 'crimped sheet' denotes a sheet having a plurality of substantially parallel ridges or corrugations. Preferably, when the aerosol-generating article has been assembled, the substantially parallel ridges or corrugations extend along or parallel to the longitudinal axis of the aerosol-generating article. This advantageously facilitates gathering of the crimped sheet of homogenised tobacco material to form the aerosol-forming substrate. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article when the aerosol-generating article has been assembled. In certain embodiments, the aerosol-forming substrate may comprise a gathered sheet of homogenised tobacco material that is substantially evenly textured over substantially its entire surface. For example, the aerosol-forming substrate may comprise a gathered crimped sheet of homogenised tobacco material comprising a plurality of substantially parallel ridges or corrugations that are substantially evenly spaced-apart across the width of the sheet.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

Although reference is made to solid aerosol-forming substrates above, it will be clear to one of ordinary skill in the art that other forms of aerosol-forming substrate may be used with other embodiments. For example, the aerosol-forming substrate may be a liquid aerosol-forming substrate. If a liquid aerosol-forming substrate is provided, the aerosol-generating device preferably comprises means for retaining the liquid. For example, the liquid aerosol-forming substrate may be retained in a container. Alternatively or in addition, the liquid aerosol-forming substrate may be absorbed into a porous carrier material. The porous carrier material may be made from any suitable absorbent plug or body, for example, a foamed metal or plastics material, polypropylene, terylene, nylon fibres or ceramic. The liquid aerosol-forming substrate may be retained in the porous carrier material prior to use of the aerosol-generating device or alternatively, the liquid aerosol-forming substrate material may be released into the porous carrier material during, or immediately prior to use. For example, the liquid aerosol-forming substrate may be provided in a capsule. The shell of the capsule preferably melts upon heating and releases the liquid aerosol-forming substrate into the porous carrier material. The capsule may optionally contain a solid in combination with the liquid.

Alternatively, the carrier may be a non-woven fabric or fibre bundle into which tobacco components have been incorporated. The non-woven fabric or fibre bundle may comprise, for example, carbon fibres, natural cellulose fibres, or cellulose derivative fibres.

The aerosol-generating device may still further comprise an air inlet. The aerosol-generating device may still further comprise an air outlet. The aerosol-generating device may still further comprise a condensation chamber for allowing the aerosol having the desired characteristics to form.

The aerosol-generating device is preferably a handheld aerosol-generating device that is comfortable for a user to hold between the fingers of a single hand. The aerosol-generating device may be substantially cylindrical in shape. The aerosol-generating device may have a polygonal cross section and a protruding button formed on one face: in this embodiment, the external diameter of the aerosol-generating device may be between about 12.7 mm and about 13.65 mm measured from a flat face to an opposing flat face; between about 13.4 mm and about 14.2 mm measured from an edge to an opposing edge (that is, from the intersection of two faces on one side of the aerosol-generating device to a corresponding intersection on the other side); and between about 14.2 mm and about 15 mm measured from a top of the button to an opposing bottom flat face. The length of the aerosol generating device may be between about 70 mm and 120 mm.

In another aspect embodiment, there is provided a method for detecting the presence of an aerosol-forming substrate close to the heater element or a material property of an aerosol-forming substrate in an aerosol generating device, the aerosol generating device comprising a heater element configured to heat an aerosol-forming substrate and a power source connected to the heater element, the method comprising:

controlling the power supplied to the heater element from the power source to maintain the temperature of the heater element at a target temperature, comparing a measure of power supplied to the heater element or energy supplied to the heater element from the power source to a threshold measure of power or energy, and determining the presence of an aerosol-forming substrate close to the heater element or a material property of an aerosol-forming substrate close to the heater element based on a result of the step of comparing.

The measure of power or energy can be any measure of power or energy, including average power over a predetermined time period or over a predetermined number of measurement cycles, a rate of change of power or energy or a cumulative measure of the power or energy supplied over a predetermined time period or over a predetermined number of measurement cycles.

In one embodiment, the measure of energy is normalised energy over a predetermined time period. In another embodiment, the measure of energy is a rate of decrease of normalised energy over a predetermined time period.

The method may further comprise the step of reducing to zero the supply of power to the heater element from the power source if the measure of power or energy is less than the threshold measure of power or energy. If the amount of energy needed to reach and maintain the heater element temperature at a target temperature is less than expected, it may be because an aerosol forming substrate is not present in the device or it may be that an unsuitable substrate, such as a previously used substrate, is in the device. In either case it is usually desirable to stop the supply of power to the heater.

The method may include the step of monitoring the temperature of the heater element based on a measure of the electrical resistance of the heater element.

In a further embodiment, there is provided a computer readable program that when executed on a computer or other suitable processing device, carries out the method described above. The specification includes embodiments that may be implemented as a software product suitable for running on an aerosol generating devices having a programmable controller as well as the other required hardware elements.

Examples will now be described in detail with reference to the accompanying drawings, in which.

Figure 1:
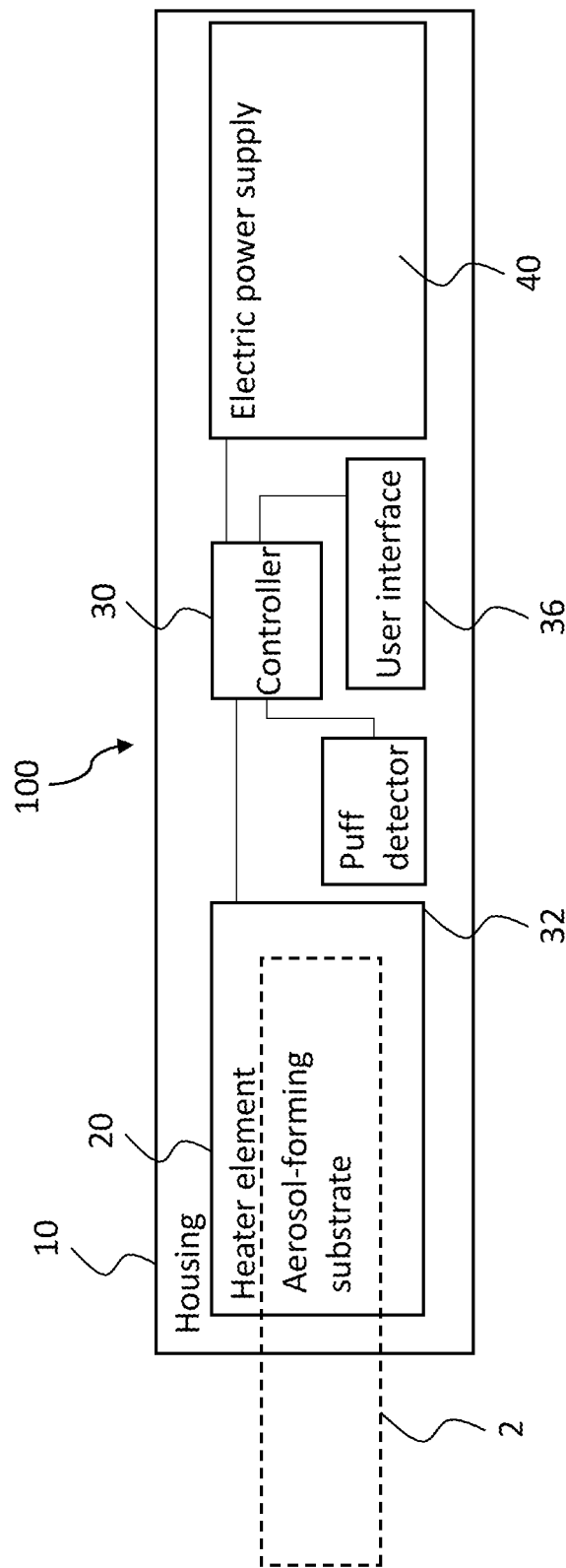
FIG. 1 is a schematic drawing showing the basic elements of an aerosol generating device in accordance with one embodiment.

In FIG. 1, the inside of an embodiment of the electrically heated aerosol generating system 100 is shown in a simplified manner. Particularly, the elements of the electrically heated aerosol generating system 100 are not drawn to scale. Elements that are not relevant for the understanding of the system have been omitted to simplify FIG. 1.

The electrically heated aerosol generating system 100 comprises a housing 10 and an aerosol-forming substrate 2, for example a cigarette. The aerosol-forming substrate 2 is pushed inside the housing 10 to come into thermal proximity with the heater element 20. The aerosol-forming substrate 2 will release a range of volatile compounds at different temperatures. Some of the volatile compounds released from the aerosol-forming substrate 2 are only formed through the heating process. Each volatile compound will be released above a characteristic release temperature. By controlling the maximum operation temperature of the electrically heated aerosol generating system 100 to be below the release temperature of some of the volatile compounds, the release or formation of these smoke constituents can be avoided.

Additionally, the housing 10 comprises an electrical energy supply 40, for example a rechargeable lithium ion battery. A controller 30 is connected to the heater element 20, the electrical energy supply 40, a puff detector 32 and a graphical user interface 36, for example a display.

The controller 30 controls the user interface 36 to display system information, for example, battery power, temperature, status of aerosol-forming substrate 2, other messages or combinations thereof.

The puff detector 32 is an optional element and detects airflow in the device, indicative of a puff being taken by a user. The puff detector signals such a puff to the controller 30. The controller 30 further controls the maximum operation temperature of the heater element 20. The temperature of the heater element can be detected by a dedicated temperature sensor. But in this embodiment the temperature of the heater element is determined by monitoring its electrical resistivity. The electrical resistivity of a length of wire is dependent on its temperature. Resistivity ρ increases with increasing temperature. The actual resistivity ρ characteristic will vary depending on the exact composition of the alloy and the geometrical configuration of the heater element 20, and an empirically determined relationship can be used in the controller. Thus, knowledge of resistivity ρ at any given time can be used to deduce the actual operation temperature of the heater element 20.

The resistance of the heater element R=V/I; where V is the voltage across the heater element and I is the current passing through the heater element 20. The resistance R depends on the configuration of the heater element 20 as well as the temperature and is expressed by the following relationship:

$$R=\rho(T)*L/S \qquad \text{equation 1}$$

Where ρ(T) is the temperature dependent resistivity, L is length and S the cross-sectional area of the heater element 20. L and S are fixed for a given heater element 20 configuration and can be measured. Thus, for a given heater element design R is proportional to ρ(T).

The resistivity ρ(T) of the heater element can be expressed in polynomial form as follows:

$$\rho(T)=\rho_o*(1+\alpha_1 T+\alpha_2 T^2) \qquad \text{equation 2}$$

Where $\rho_o$ is the resistivity at a reference temperature $T_o$ and $\alpha_1$ and $\alpha_2$ are the polynominal coefficients.

Thus, knowing the length and cross-section of the heater element 20, it is possible to determine the resistance R, and therefore the resistivity ρ at a given temperature by measuring the heater element voltage V and current I. The temperature can be obtained simply from a look-up table of the characteristic resistivity versus temperature relationship for the heater element being used or by evaluating the polynomial of equation (2) above. Preferably, the process may be simplified by representing the resistivity ρ versus temperature curve in one or more, preferably two, linear approximations in the temperature range applicable to tobacco. This simplifies evaluation of temperature which is desirable in a controller 30 having limited computational resources.

Figure 2:
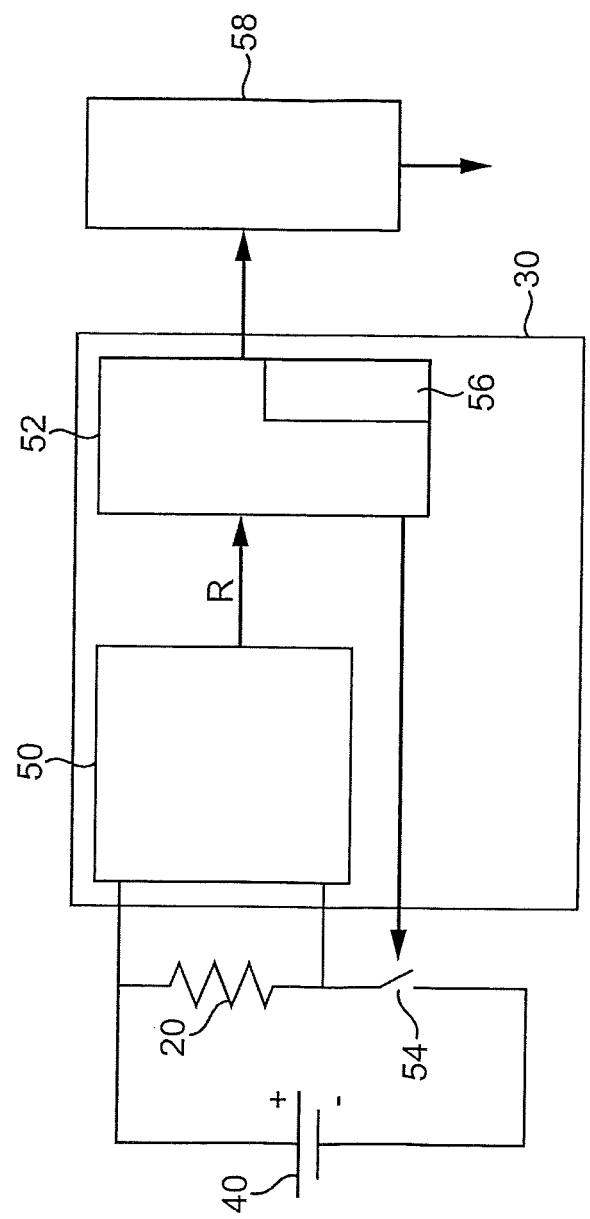
FIG. 2 is a schematic diagram illustrating the control elements of one embodiment.

FIG. 2 is a block diagram illustrating the control elements of the device of FIG. 1. FIG. 2 also shows the connection of the aerosol-generating device to an external device 58. The controller 30 includes a measurement unit 50 and a control unit 52. The measurement unit is configured to determine the resistance R of the heater element 20.

The measurement unit 50 passes resistance measurements to the control unit 52. The control unit 52 then controls the provision of power from the battery 40 to the heater element 20 by toggling switch 54. The controller may comprise a microprocessor as well as discrete electronic components.

In a preparation of the controlling of the temperature, a value for the target operation temperature of the electrically heated aerosol generating system 100 is selected. The selection is based on the release temperatures of the volatile compounds that should and should not be released. This predetermined value is then stored in the control unit 52. The control unit 52 includes a non-volatile memory 56.

The controller 30 controls the heating of the heater element 20 by controlling the supply electrical energy from the battery to the heater element 20. By the switching of switch 54, power is provided as a pulsed signal. The pulse width or duty cycle of the signal can be modulated by the control unit 52 to alter the amount of energy supplied to the heater element.

In use, the controller 30 measures the resistivity ρ of the heater element 20. The controller 30 then converts the resistivity of the heater element 20 into a value for the actual operation temperature of the heater element, by comparing the measured resistivity ρ with the look-up table. This may be done by the measurement unit 50 or by the control unit 52. In the next step, the controller 30 compares the derived actual operation temperature with the target operation temperature. If the actual operation temperature is below the target operation temperature, the control unit 52 supplies the heater element 20 with additional electrical energy in order to raise the actual operation temperature of the heater element 20. If the actual operation temperature is above the target operation temperature, the control unit 52 reduces the electrical energy supplied to the heater element 20 in order to lower the actual operation temperature back to the target operation temperature.

The control unit may implement any suitable control technique to regulate the temperature, such as a simple thermostatic feedback loop or a proportional, integral, derivative (PID) control strategy.

Figure 3:
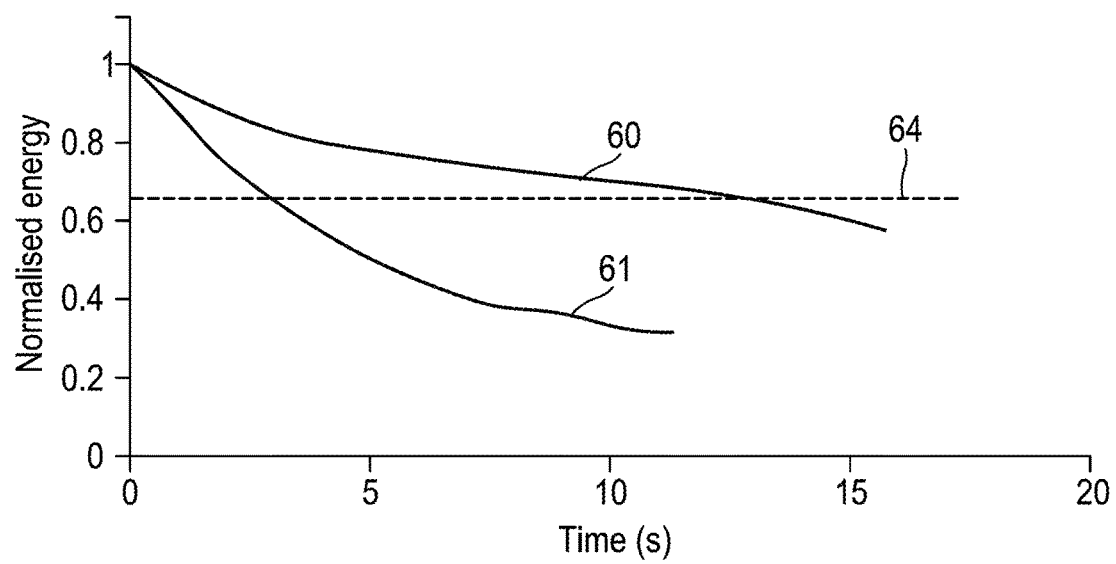
FIG. 3 is a graph illustrating the different the normalised energy required to be supplied to a heater element to maintain the temperature at a target level for new, old and no substrate next to the heater element.

The amount of energy required to reach the target temperature and maintain the heater element at the target temperature depends on the presence or absence of a substrate material 2 close to the heater element 20, and on the properties of the substrate. FIG. 3 shows the evolution of normalised energy supplied to the heater element as a function of time. Curve 60 is the normalised energy when a new substrate is in the device and curve 61 is the normalised energy when no substrate is in the device. The normalised energy is the energy supplied during a fixed time interval normalised against an initial energy measurement. A normalised measure of energy minimises the influence of environmental conditions such as ambient temperature, airflow and humidity.

It can be seen that in both cases the power delivered to heater element monotonically decreases with time following an initial high power period to bring the heater element up to the target temperature. However, FIG. 3 shows that at T=10 seconds the amount of energy supplied with a new substrate in the device is about twice the amount of energy supplied when no substrate is present in the device. The difference in energy supplied between a new and a previously heated substrate is smaller but still detectable. In one embodiment, the difference in the normalized energy may be measured at T=5 seconds and accurately determine if a substrate is present or not.

The controller is able to calculate the normalised energy supplied to the heater element up to a predetermined time, and from that is able to determine if an expected or proper substrate is in the device.

Figure 4:
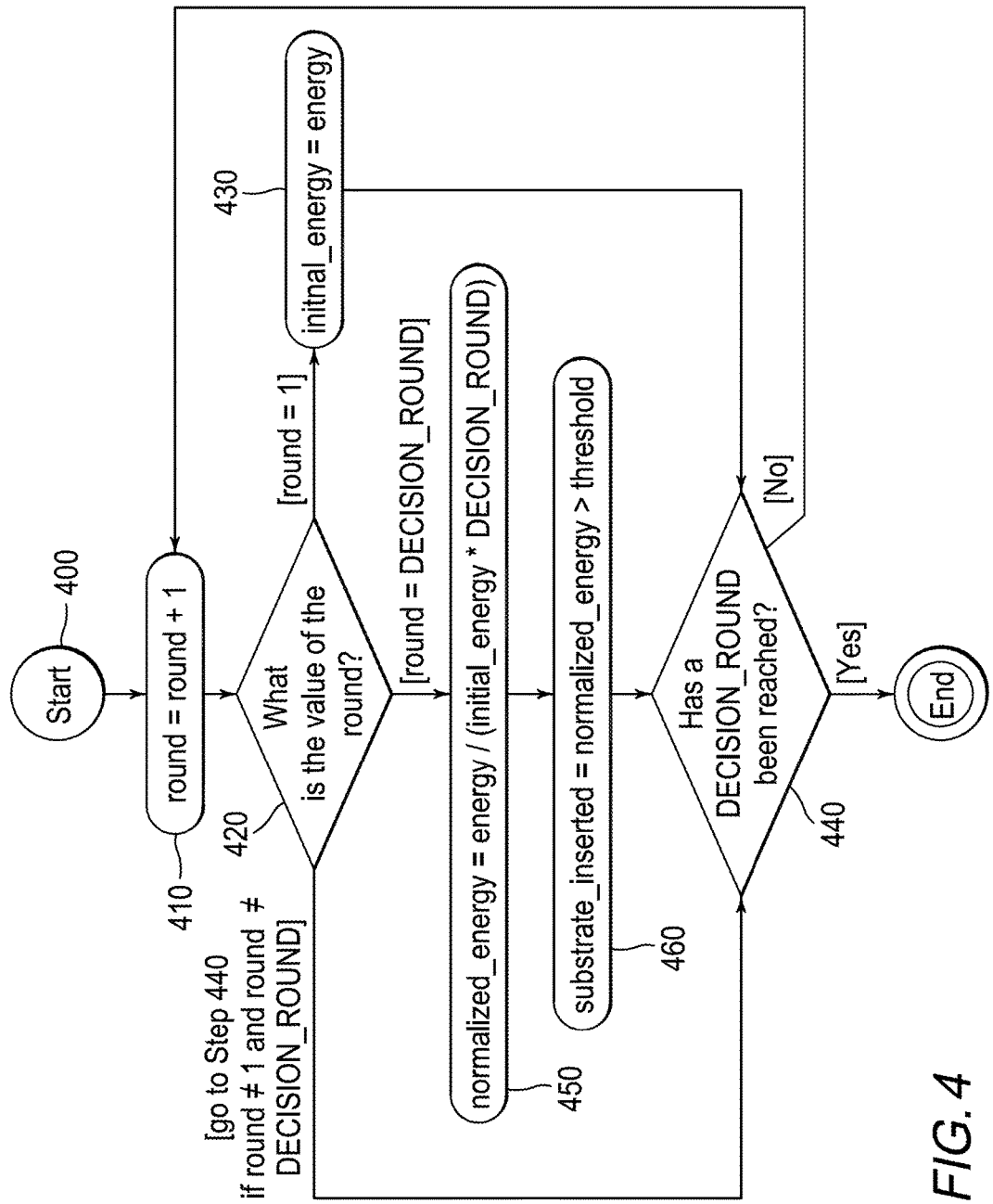
FIG. 4 illustrates a control sequence for determining if an appropriate substrate is present in the device.

FIG. 4 illustrates an example of a control process that can be carried out by the control unit 52 to determine if a substrate is in the device or not. The process is a loop process and starts at step 400. In step 410 the round number is incremented. At the start of the process the round number is set to zero. Each time the control loop is passed through, the round number is incremented in step 410. At step 420 the process branches depending on the value of the round number. In the initial loop, when the round number equals one, the process passes to step 430. At step 430 the initial energy, i.e. the energy supplied to the heater so far, is set as the energy. This initial energy is used to normalise subsequent energy measurements. The process then passes to step 440 and back to step 410. Subsequent rounds pass directly from step 420 to step 440 until a decision round is reached. Each round may be carried out at a fixed time interval, for example every two seconds. The decision round corresponds to the time at which the controller is configured to compare the normalised energy with an expected or threshold value to determine if a substrate is present or not. The threshold value of normalised energy is illustrated by dotted line 64 in FIG. 3. In this example the decision round is round five, and occurs 10 seconds after the device is switched on. In the decision round, the process passes from step 420 to step 450. In step 450 the normalised energy is calculated as the energy supplied since the device was switched on divided by the product of the initial energy and the decision round number (in this example five). The calculated normalised energy is then compared to a threshold value in step 460. If the normalised energy exceeds the threshold value then the control unit determines that an appropriate substrate is present and the device can continue to be used. If the normalised energy does not exceed the threshold, the control unit determines that no substrate (or an inappropriate substrate) is present and the control unit then prevents the supply of power to the heater element by holding switch 54 open.

The process illustrated in FIG. 4 is just one example of a process for determining if an appropriate substrate is present in an aerosol generating device. Other measures of power or energy supplied to the heater element may be used and normalised or non-normalised data may be used. The time at which the determination is made is also a matter of choice. The advantage of an early determination in order to take early action if necessary must be balanced against the need to obtain a reliable result.

The measure of power or energy can be compared to a plurality of thresholds. This may be useful to distinguish between different types of substrate or between an inappropriate substrate and the absence of any substrate.

As well as being useful for dynamic control of the aerosol generating device, the substrate detection data determined by the controller 30 may be useful for analysis purposes in clinical trials. FIG. 2 illustrates connection of the controller 30 to an external device 58. The substrate detection data can be exported to the external device 58 (together with any other captured data) and may be further relayed from the device 58 to other external processing or data storage devices. The aerosol generating device may include any suitable data output means. For example the aerosol generating device may include a wireless radio connected to the controller 30 or memory 56, or a universal serial bus (USB) socket connected to the controller 30 or memory 56. Alternatively, the aerosol generating device may be configured to transfer data from the memory to an external memory in a battery charging device every time the aerosol generating device is recharged through suitable data connections. The battery charging device can provide a larger memory for longer term storage of the puff data and can be subsequently connected to a suitable data processing device or to a communications network.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. An aerosol generating device, comprising:
   a heater element configured to heat an aerosol-forming substrate, the aerosol-forming substrate being movable inside the aerosol generating device to come into thermal proximity with the heater element;
   a power source connected to the heater element; and
   a controller connected to the heater element and to the power source, and comprising circuitry configured to:
   control power supplied to the heater element from the power source to maintain a temperature of the heater element at a target temperature,
   compare a measure of the power supplied to the heater element or energy supplied to the heater element from the power source to a threshold measure of power or energy, and
   detect a presence of the aerosol-forming substrate close to the heater element or a material property of the aerosol-forming substrate close to the heater element, and detect an absence of the aerosol-forming substrate from the aerosol generating device, based on the compared measure of the power or the energy supplied to the heater element.

2. The aerosol generating device according to claim 1, wherein the measure of energy is normalised energy or a rate of decrease of normalised energy over a predetermined time period.

3. The aerosol generating device according to claim 1, wherein the controller is configured to reduce to zero the supply of power to the heater element from the power source if the measure of power or energy is less than the threshold measure of power or energy.

4. The aerosol generating device according to claim 1, wherein the aerosol generating device is configured to receive the aerosol-forming substrate into contact with the heater element.

5. The aerosol generating device according to claim 1, wherein the controller is configured to monitor the temperature of the heater element based on a measure of the electrical resistance of the heater element.

6. The aerosol generating device according to claim 1, wherein the aerosol generating device is an electrical smoking device.

7. The aerosol generating device according to claim 1, wherein the aerosol generating device includes a data output port and wherein the controller is configured to provide to the data output port a record of the detected presence of the aerosol-forming substrate close to the heater element or the material property of the aerosol-forming substrate close to the heater element.

8. The aerosol generating device according to claim 7, wherein the controller is configured to provide to the data output port during a charging operation of the power source a record of the detected presence of the aerosol-forming substrate close to the heater element or the material property of the aerosol-forming substrate close to the heater element.

9. A method for detecting a presence of an aerosol-forming substrate close to a heater element or a material property of the aerosol-forming substrate in an aerosol generating device, the aerosol generating device comprising the heater element configured to heat the aerosol-forming substrate, wherein the aerosol-forming substrate is movable inside the aerosol generating device to come into thermal proximity with the heater element, and a power source connected to the heater element, the method comprising:

controlling power supplied to the heater element from the power source to maintain a temperature of the heater element at a target temperature;

comparing a measure of the power supplied to the heater element or energy supplied to the heater element from the power source to a threshold measure of power or energy; and determining a presence of the aerosol-forming substrate close to the heater element or a material property of the aerosol-forming substrate close to the heater element based on a result of the step of comparing, and detecting an absence of the aerosol-forming substrate from the aerosol generating device, based on the compared measure of the power or the energy supplied to the heater element.

10. The method according to claim 9, further comprising the step of reducing to zero the supply of power to the heater element from the power source if the measure of power or energy is less than the threshold measure of power or energy.

11. The method according to claim 9, wherein the measure of energy is normalised energy or a rate of decrease of normalised energy over a predetermined time period.

12. The method according to claim 9, further comprising the step of monitoring the temperature of the heater element based on a measure of the electrical resistance of the heater element.

13. A non-transitory computer readable storage medium having a computer program stored thereon that when executed on a computer, causes the computer to carry out the method of claim 9.

* * * * *